(12) United States Patent
Rokicki et al.

(10) Patent No.: US 8,546,297 B2
(45) Date of Patent: Oct. 1, 2013

(54) METHOD FOR PREPARING AN EPOXIDATION CATALYST

(75) Inventors: Andrzej Rokicki, Mountain Lakes, NJ (US); Arie Bortinger, Ridgewood, NJ (US); Christelle Verrier, Little Ferry, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 104 days.

(21) Appl. No.: 13/109,657

(22) Filed: May 17, 2011

(65) Prior Publication Data

US 2011/0301367 A1    Dec. 8, 2011

Related U.S. Application Data

(60) Provisional application No. 61/345,466, filed on May 17, 2010.

(51) Int. Cl.
| | | |
|---|---|---|
| *B01J 23/48* | (2006.01) | |
| *B01J 23/50* | (2006.01) | |
| *B01J 23/58* | (2006.01) | |
| *C07D 301/10* | (2006.01) | |

(52) U.S. Cl.
USPC .......................... 502/347; 502/330; 549/534

(58) Field of Classification Search
USPC .................. 502/347, 348, 330; 549/534
See application file for complete search history.

(56) References Cited

U.S. PATENT DOCUMENTS

| | | |
|---|---|---|
| 2,125,333 A | 8/1938 | Carter |
| 2,615,900 A | 10/1952 | Sears |
| 2,773,844 A | 12/1956 | Carlson et al. |
| 3,575,888 A | 4/1971 | Long |
| 3,702,359 A | 11/1972 | Dulmage et al. |
| 3,962,136 A | 6/1976 | Nielsen et al. |
| 4,005,049 A | 1/1977 | Fields |
| 4,010,115 A | 3/1977 | Niesen et al. |
| 4,761,394 A | 8/1988 | Lauritzen |
| 4,766,105 A | 8/1988 | Lauritzen |
| 4,908,343 A | 3/1990 | Bhasin |
| 4,916,243 A | 4/1990 | Bhasin et al. |
| 5,011,807 A | 4/1991 | Hayden et al. |
| 5,057,481 A | 10/1991 | Bhasin |
| 5,099,041 A | 3/1992 | Hayden et al. |
| 5,102,848 A | 4/1992 | Soo et al. |
| 5,112,795 A | 5/1992 | Minahan et al. |
| 5,187,140 A | 2/1993 | Thorsteinson et al. |
| 5,407,888 A | 4/1995 | Herzog et al. |
| 5,444,034 A | 8/1995 | Rizkalla |
| 5,504,052 A | 4/1996 | Rizkalla et al. |
| 5,545,603 A | 8/1996 | Kemp |
| 5,646,087 A | 7/1997 | Rizkalla et al. |
| 7,102,022 B2 | 9/2006 | Evans et al. |
| 2004/0049061 A1 | 3/2004 | Lockemeyer et al. |
| 2006/0252639 A1 | 11/2006 | Pak et al. |
| 2007/0185339 A1 | 8/2007 | Lu |
| 2007/0225511 A1 * | 9/2007 | Bortinger et al. ............. 549/536 |
| 2008/0039316 A1 | 2/2008 | Bhise et al. |
| 2008/0081920 A1 * | 4/2008 | Gueckel ........................ 549/533 |

FOREIGN PATENT DOCUMENTS

EP    1081116 A1    3/2001

OTHER PUBLICATIONS

International Search Report dated Jan. 18, 2012 received in a corresponding foreign application.

* cited by examiner

*Primary Examiner* — Anthony J Zimmer

(74) *Attorney, Agent, or Firm* — Scully, Scott, Murphy & Presser, P.C.

(57) ABSTRACT

A process for the preparation of a catalyst useful for the vapor phase production of ethylene oxide from ethylene and oxygen comprising the steps of providing a catalyst precursor comprising an inert support having a catalytically effective amount of a silver containing compound, a promoting amount of an alkali metal containing compound, and a promoting amount of a transition metal containing compound disposed thereon; and heating the catalyst precursor in a gas atmosphere for a first period of time and a second period of time, wherein for the first period of time the gas atmosphere is an inert gas atmosphere and the temperature range is from about 25° C. to about 600° C., and then in a second period of time the gas atmosphere is an oxygen-containing atmosphere and the second period temperature range is from about 350° C. to about 600° C.

24 Claims, No Drawings

METHOD FOR PREPARING AN EPOXIDATION CATALYST

CROSS REFERENCE TO RELATED APPLICATION

This application claims benefit of U.S. Provisional Patent Application Ser. No. 61/345,466, filed May 17, 2010, the entire content and disclosure of which is incorporated herein by reference.

FIELD OF THE INVENTION

This invention relates to silver catalysts useful for the production of an alkylene oxide, their preparation, and their use in alkylene oxide processes. More particularly, the invention relates to a method of preparing a supported, metal promoted silver catalyst capable of oxidizing an alkene, preferably ethylene, with an oxygen containing gas in the vapor phase to produce alkylene oxide, preferably ethylene oxide, at high efficiencies and selectivities.

BACKGROUND OF THE INVENTION

It is known in the art to produce supported silver catalysts for the conversion of ethylene and oxygen to ethylene oxide. Many modifications have been proposed to improve the activity and selectivity of these catalysts. These modifications have involved improvements to the supports employed, the methods of production, the physical form of the silver on the support and the inclusion of additives to the catalyst composition. Methods are known for the preparation of supported silver catalysts useful for the vapor phase oxidation of ethylene to ethylene oxide, which involve impregnating a support such as alumina with a silver salt/amine solution. U.S. Pat. No. 3,702,359 is illustrative of such procedures.

U.S. Pat. No. 2,125,333 discloses the use of alkali metals, including sodium or potassium and their salts as additives for various silver ethylene oxide catalysts. U.S. Pat. No. 2,615,900 cites a large number of useful promoters for silver catalysts. U.S. Pat. No. 2,773,844 discloses a multi-step silver deposition process for preparing a silver based catalyst. U.S. Pat. No. 3,575,888 discloses the use of aluminum oxide supports having a pore volume between about 0.15 and 0.30 $m^2/gm$ and surface area below about 10 $m^2/gm$. The use of small amounts of alkali metals, K, Rb and Cs, were noted as useful promoters in supported silver catalysts. See, for example, U.S. Pat. Nos. 3,962,136 and 4,010,115.

U.S. Pat. No. 4,005,049 teaches the preparation of a silver/transition metal catalyst useful in oxidation reactions. In the '049 patent, catalytically active metals such as Ag and Re are co-sputtered along with a co-sputtered support material on a particular support. The preparation of silver catalysts which also contain alkali metal promoters by analogous procedures is shown, for example, in U.S. Pat. No. 3,962,136. Similar procedures for the preparation of silver catalysts promoted by an alkali metal and rhenium and also with a co-promoter selected from sulfur, molybdenum, tungsten, chromium and mixtures are disclosed, for example, in U.S. Pat. No. 4,766,105.

Catalyst preparation by these prior art procedures has involved impregnating a support with a silver/amine solution which may contain various promoters, and thereafter heating the impregnated support in a forced air oven up to a temperature of about 275° C. in order to reduce the silver to metallic silver and to separate volatiles from the catalyst. This step of reducing the silver to metallic silver is typically referred to in the art as calcination.

U.S. Pat. No. 4,916,243 show silver catalysts for ethylene oxidation to ethylene oxide prepared by impregnating an inert support with a silver/amine and silver lactate solutions. The impregnated carriers were then heat treated on a steel belt transported through a 2"×0.2" square heating zone for 2.5 minutes, the heating zone being maintained at 500° C. by passing hot air upward through the belt, or at 400° C. for 4 minutes.

U.S. Pat. No. 5,444,034 relates to silver catalyst preparation wherein a support is impregnated with a hydrocarbon solution of a silver salt of an organic acid and activated in stages up to a temperature of 500° C. under an inert gas such as nitrogen.

In other descriptions of processes of ethylene oxide production, addition of oxygen-containing gases to the feed increased the efficiency. In U.S. Pat. No. 5,112,795, for example, 5 ppm of nitric oxide was added to the gas feed of composition: 8 volume % oxygen, 30 volume % ethylene, about 5 ppm ethyl chloride and the balance nitrogen.

U.S. Pat. Nos. 5,504,052 and 5,646,087 show silver catalysts for ethylene oxidation to ethylene oxide prepared by impregnating an inert support with a silver/amine solution as well as with various promoters and calcining the impregnated support at a range between 300° C. to 500° C., while the catalyst is maintained under an inert atmosphere.

In the other processes to increase efficiency, particularly selectivity, the silver catalysts were treated at a certain temperature and a certain gas mixture. For example in U.S. Patent Application Publication No. 2004/0049061 and U.S. Pat. No. 7,102,022 the selectivity of a highly selective epoxidation catalyst can be improved by heat-treating the catalyst in the presence of oxygen at a temperature which is typically above the catalyst's normal initial operation temperature. Typically, the heat-treating temperature is greater than 250° C. and contact occurs for a period of time up to 150 hours. Such treatment, which is performed under conditions different than regular production, will necessarily interfere with productivity of the given operation leading to reduced profitability of the plant.

U.S. Patent Application Publication No. 2007/0185339 discloses a process for treating a supported epoxidation catalyst which comprises contacting the catalyst or a precursor of the catalyst comprising silver in cationic form with a treatment feed comprising oxygen at a catalyst temperature of at least 350° C. for a duration of at least 5 minutes.

Thus, the prior art teaches catalyst preparation by calcining an impregnated support either in air, i.e., a large amount of oxygen, or under an inert atmosphere such as nitrogen.

In U.S. Patent Publication No. 2006/0252639, it is disclosed that the calcination of an impregnated support in an inert atmosphere, such as nitrogen, with the addition of only a small amount of an oxidizing gas, such as molecular oxygen in the inert atmosphere, improves the effective life, activity and selectivity of an ethylene oxide catalyst.

Specifically, the '639 publication provides a procedure for the preparation of a catalyst useful for the vapor phase production of ethylene oxide from ethylene and oxygen which comprises impregnating an inert support with a solution comprising a catalytically effective amount of a silver containing compound, a promoting amount of an alkali metal containing compound, and a promoting amount of a transition metal containing compound; calcining the impregnated support by heating the impregnated support at a temperature of from about 200° C. to about 600° C. for a time sufficient to convert the silver in the silver containing compound to metallic silver and to decompose and remove substantially all organic materials; the heating being conducted under an atmosphere comprising a combination of an inert gas and from about 10 ppm to about 5% by volume of a gas of an oxygen containing oxidizing component.

Although the calcination described in the '639 publication provides improvements over prior art calcination processes, indiscriminate addition of oxygen to an inert gas might, under some circumstances, lead to undesirable combustion rather than thermal decomposition of the catalyst precursor with negative consequences for catalyst performance. Moreover, in order to prevent open flame combustion in the system during calcination, the calcination process disclosed in the '639 publication is limited to 5 vol. % of an oxygen containing oxidizing component. This, depending on the specific formulation of the silver catalysts, may not be sufficient to fully and efficiently condition the catalyst.

In view of the above, there is a need for providing a calcination procedure that improves catalyst performance without experiencing any problems with respect to open flame combustion. Also, there is a need for providing a calcination procedure that requires no special treatment or time to start-up the catalyst which would result in improved economics for the operator.

SUMMARY OF THE INVENTION

The present invention relates to a process for the preparation of a catalyst useful for the vapor phase production of ethylene oxide from ethylene and oxygen comprising the steps of providing a catalyst precursor comprising an inert support having a catalytically effective amount of a silver containing compound, a promoting amount of an alkali metal containing compound, and a promoting amount of a transition metal containing compound disposed thereon; and heating the catalyst precursor in a gas atmosphere for a first period of time and a second period of time, wherein for the first period of time the gas atmosphere is an inert gas atmosphere and the temperature range is from about 25° C. to about 600° C., and then in a second period of time the gas atmosphere is an oxygen-containing atmosphere and the second period temperature range is from about 350° C. to about 600° C.

DETAILED DESCRIPTION OF THE INVENTION

The present invention, which provides a process for preparing a silver catalyst useful for production of an alkylene oxide, will now be described in greater detail.

As stated above, the present invention provides a process for the preparation of a catalyst useful for the vapor phase production of ethylene oxide from ethylene and oxygen. The inventive process includes first providing a catalyst precursor including an inert support having a catalytically effective amount of a silver containing compound, a promoting amount of an alkali metal containing compound, and a promoting amount of a transition metal containing compound disposed thereon. Finally, the catalyst precursor is heated in a gas atmosphere, where the content of the atmosphere and the temperature is altered over the course of the heating. During a first period of time the gas atmosphere is an inert gas atmosphere and the temperature range is maintained from about 25° C. to about 600° C. for a time period of about 1 minute to about 45 minutes. This first period occurs for a sufficiently long period of time to obtain calcination in the catalyst precursor by converting the silver in the silver containing compound to metallic silver and to decompose and remove substantially all organic materials. After this first period of time, the gas atmosphere is changed to an oxygen-containing atmosphere, and the temperature is maintained within the range of about 350° C. to about 600° C. for a time period of about 30 seconds to about 45 minutes.

The silver catalysts of the invention are prepared by impregnating a porous refractory support with silver ions, compounds, complexes and/or salts dissolved in a suitable solvent sufficient to cause deposition of silver precursor compound onto the support. The impregnated carrier is then removed from the solution and the deposited silver compound is reduced to metallic silver by the two-step calcination procedure described hereinbelow. Also deposited on the support either prior to, coincidentally with, or subsequent to the deposition of the silver are suitable ions, compounds and/or salts of an alkali metal dissolved in a suitable solvent. Also deposited on the carrier either prior to, coincidentally with, or subsequent to the deposition of the silver and/or alkali metal are suitable transition metal ions, compounds, complexes and/or salts dissolved in an appropriate solvent.

The support or carrier used for these catalysts may be a porous refractory catalyst carrier or support material which is relatively inert in the presence of the ethylene oxidation feed materials, products and reaction conditions. Such conventional materials are known to those skilled in the art and may be of natural or synthetic origin and preferably are of a macroporous structure, that is, a structure having a surface area of about 10 $m^2/g$ or less and preferably about 3 $m^2/g$ or less. Examples of supports that are useful as supports for the ethylene oxide catalysts of this invention are aluminum oxides, especially alpha alumina, charcoal, pumice, magnesia, zirconia, keiselguhr, fullers' earth, silicon carbide, porous agglomerates comprising silica and/or silicon carbide, silica, magnesia, selected clays, artificial and natural zeolites and ceramics. Preferred catalysts may be made with supports comprising alumina, silica, silica-alumina or combinations thereof.

Most preferred supports are those principally containing alpha alumina, particularly those containing up to about 15 wt % silica. In the case of alpha alumina containing supports, preferred are those having a surface area, as measured by the B.E.T. method, from about 0.03 $m^2/g$ to about 10 $m^2/g$, preferably from about 0.05 $m^2/g$ to about 5 $m^2/g$, more preferably from about 0.1 $m^2/g$ to about 3 $m^2/g$, and a water pore volume, as measured by conventional water absorption techniques, from about 0.1 cc/g to about 0.75 cc/g by volume, preferably from about 0.25 cc/g to about 0.55 cc/g. The B.E.T. method for determining specific surface area is described in detail in Brunauer, S., Emmett, P. H. and Teller, E., J. Am. Chem. Soc., 60, 309-16 (1938). Pore volume and the pore size distribution are measured by a conventional mercury porosimeter method; see Drake and Ritter, "Ind. Eng. Chem. Anal. Ed.," 17, 787 (1945). Such carriers are commercially available from various carrier manufactures including, for example, the Norton Company.

For use in commercial ethylene oxide production applications, the supports are desirably formed into regularly shaped pellets, spheres, rings, particles, chunks, pieces, pellets, wagon wheels, and the like of a size suitable for employment in fixed bed reactors. Desirably, the support particles may have "equivalent diameters" in the range from about 3 mm to about 10 mm and preferably in the range from about 4 mm to about 9 mm, which are usually compatible with the internal diameter of the tube reactors in which the catalyst is placed. "Equivalent diameter" is the diameter of a sphere having the same external surface (i.e., neglecting surface within the pores of the particle) to volume ratio as the support particles being employed.

A conventional porous refractory support as described above is impregnated with a silver impregnating solution, preferably an aqueous silver solution. The support is also impregnated at the same time or in a separate step (or steps) with various catalyst promoters. Preferred catalysts prepared in accordance with this invention contain up to about 45% by weight of silver, expressed as metal, deposited upon the surface and throughout the pores of a porous refractory support. Silver contents, expressed as metal, of about 1 to about 40% based on weight of total catalyst are preferred, while silver contents from about 8 to about 35% are more preferred.

The amount of silver deposited on the support or present on the support is that amount which is a catalytically effective amount of silver, i.e., an amount which economically catalyzes the reaction of ethylene and oxygen to produce ethylene oxide. As used herein, the term "catalytically effective amount of silver" refers to an amount of silver that provides a measurable conversion of ethylene and oxygen to ethylene oxide and selectivity and activity stability within catalyst life.

Useful silver containing compounds non-exclusively include silver oxalate, silver nitrate, silver oxide, silver carbonate, a silver carboxylate, silver citrate, silver phthalate, silver lactate, silver propionate, silver butyrate and higher fatty acid salts and combinations thereof.

The catalyst of the invention comprises a catalytically effective amount of silver, a promoting amount of alkali metal, a promoting amount of a transition metal supported on a porous, refractory support. As used herein the term "promoting amount" of a certain component of a catalyst refers to an amount of that component that works effectively to provide an improvement in one or more of the catalytic properties of that catalyst when compared to a catalyst not containing said component. The exact concentrations employed, of course, will depend upon, among other factors, the desired silver content, the nature of the support, the viscosity of the liquid, and solubility of the silver compound.

In addition to silver, the catalyst thus also contains an alkali metal promoter selected from lithium, sodium, potassium, rubidium, cesium or combinations thereof, with, cesium being preferred. In one embodiment, both Li and Cs are employed. The amount of alkali metal deposited on the support or catalyst or present on the support or catalyst is to be a promoting amount. Preferably the amount will range from about 10 ppm to about 3000 ppm, more preferably from about 15 ppm to about 2000 ppm and even more preferably from about 20 ppm to about 1500 ppm and yet even more preferably from about 50 ppm to about 1000 ppm by weight of the total catalyst, measured as the metal.

As indicated above, the catalyst also contains a transition metal promoter which comprises an element from Groups 5b, 6b, 7b and 8 of the Periodic Table of the Elements, and combinations thereof. The amount of transition metal promoter deposited on the support or catalyst or present on the support or catalyst is to be a promoting amount. The transition metal promoter may be present in an amount from about 0.1 micromoles per gram to about 10 micromoles per gram, preferably from about 0.2 micromoles per gram to about 5 micromoles per gram, and more preferably from about 0.5 micromoles per gram to about 4 micromoles per gram of total catalyst, expressed as the metal.

The silver solution used to impregnate the support may also comprise an optional solvent or complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles of ethylene diamine per mole of silver, preferably from about 0.2 to about 4.0 moles, and more preferably from about 0.3 to about 3.0 moles of ethylene diamine for each mole of silver.

When a solvent is used, it may be water-based, or organic-based, and may be polar or substantially or totally non-polar. In general, the solvent should have sufficient solvating power to solubilize the solution components. At the same time, it is preferred that the solvent be chosen to avoid having an undue influence on, or interaction with, the solvated promoters. Examples of organic-based solvents include, but are not limited to, alcohols, in particular alkanols; glycols, in particular alkyl glycols; ketones; aldehydes; amines; tetrahydrofuran; nitrobenzene; nitrotoluene; glymes, in particular glyme, diglyme and tetraglyme; and the like. Organic-based solvents which have 1 to about 8 carbon atoms per molecule are preferred. Mixtures of organic solvents, or of water and one or more organic solvents may be used, provided that such mixed solvents function as desired herein.

The concentration of silver salt in the solution is in the range from about 0.1% by weight to the maximum permitted by the solubility of the particular salt/solubilizing agent combination employed. It is generally very suitable to employ silver salts solutions containing from about 0.5% to about 45% by weight of silver with silver concentrations from about 5 to about 35% by weight being preferred.

The catalyst may further comprise a promoting amount of one or more sulfur components, one or more fluorine containing components, or combinations thereof.

Impregnation of the selected support is achieved in conventional manners by excess solution impregnation, incipient wetness, etc. Typically, the support material is placed in the silver solution until a sufficient amount of the solution is absorbed by the support. Preferably the quantity of the silver solution used to impregnate the porous support is no more than is necessary to fill the pore volume of the porous support. The silver containing liquid penetrates by absorption, capillary action and/or vacuum into the pores of the support. A single impregnation or a series of impregnations, with or without intermediate drying, may be used, depending in part on the concentration of the silver salt in the solution. Impregnation procedures are described for example, in U.S. Pat. Nos. 4,761,394, 4,766,105, 4,908,343, 5,057,481, 5,187,140, 5,102,848, 5,011,807, 5,099,041 and 5,407,888, which are incorporated herein by reference. Known prior procedures of pre-deposition, co-deposition and post-deposition of various the promoters can be employed.

Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement shows up in the activity rather than the selectivity and an operator of an ethylene oxide plant will intentionally change the operating conditions in order to take advantage of certain catalytic properties even at the expense of other catalytic properties in order to optimize conditions and results by taking into account feedstock costs, energy costs, by-product removal costs and the like. The particular combination of silver, support, alkali metal promoter, and transition metal promoter of the instant invention will provide an improvement in one or more catalytic properties over the same combination of silver and support and none, or only one promoter.

The above description provides details concerning the catalyst precursor including an inert support having a catalytically effective amount of a silver containing compound, a promoting amount of an alkali metal containing compound, and a promoting amount of a transition metal containing compound disposed thereon that can be used in the present invention. Next, the catalyst precursor is subjected to a heating step in a gas atmosphere, where the content of the atmosphere is altered over the course of the heating. At the beginning of the heating, for a first period of time the catalyst precursor is treated under conditions to accomplish calcination, viz., to convert the silver in the silver containing compound to metallic silver and to decompose and remove substantially all organic materials. The length of the first period is from about 1 minutes to about 45 minutes, preferably about 5 minutes to about 40 minutes, and the temperature during this time is from about 25° C. to about 600° C., preferably about 25° C. to about 550° C. In terms of the length of calcination, generally the higher the temperature, the shorter the required heating period.

By "inert gas atmosphere" it is meant an atmosphere that does not react with the components of the catalyst precursor. Typical inert ambients include He, Ar, Ne, Xe, $N_2$ and mixtures thereof such as, for example, He—Ar, and He—$N_2$. In a highly preferred embodiment of the present invention, the first heating is performed in $N_2$.

At the end of the first period of the heating step, the heating continues for a second period but the gas atmosphere is changed to an oxygen-containing atmosphere. The temperature in the second period is from about 350° C. to about 600° C., preferably about 350° C. to about 550° C. The length of the second period is from about 0.5 minutes to about 45 minutes, preferably about 1 minute to about 35 minutes. It is important that substantially all of the silver compound be converted to silver and substantially all of the organic materials and organic complexes including organic silver compounds (such as silver oxalate) be decomposed during the first period of time because failing to do this before exposure of the catalyst to oxygen in the second period of time could result in open flame combustion of the remaining organics.

The reaction pressure during the heating step is in the range from about 0.1 mbar to about 5 bar, with a reaction pressure from about 0.1 mbar to about 2 bar being more preferred.

The gas of an oxygen-containing atmosphere may include air, molecular oxygen, $CO_2$, NO, $NO_2$, $N_2O_3$, $N_2O_4$, or $N_2O_5$, or a substance capable of forming NO, $NO_2$, $N_2O_3$, $N_2O_4$, or $N_2O_5$ under calcining conditions, or combinations thereof, and optionally comprising $SO_3$, $SO_2$, $P_2O_5$, $P_2O_3$ or combinations thereof. Of these, air and molecular oxygen are preferred and most preferred is air. In some embodiments, the oxygen-containing atmosphere may include an inert gas in an amount from 5 ppm to about 21% by vol.

In a useful embodiment, the atmosphere during the second period of the heating step comprises from greater than about 50% to about 100% by volume of a gas of an oxygen-containing component. In another useful embodiment, the atmosphere comprises from about 0.5% to about 21% of a gas of an oxygen-containing component.

The heating step described above may be accomplished in any type of heating apparatus or furnace. It is preferable to use gradual, step-wise heating for heating. In step-wise heating the catalyst precursor is placed on a moving belt that moves through a furnace with multiple heating zones so that the catalyst precursor enters the furnace and then passes through one or more zones of gradually increasing temperature until a maximum temperature is reached; this maximum temperature may be maintained through one or more subsequent zones. Optionally, the catalyst precursor/catalyst may be cooled to ambient temperature before exiting the furnace.

In an embodiment of the present invention making use of a multiple heating zone furnace, the catalyst precursor is subjected for a first period of time to inert gas heating in an inert gas atmosphere. The inert gas heating occurs in at least one inert gas heating zone, optionally the at least one heating zone may include two, three, four, five, six, seven or eight heating zones. The at least one inert gas heating zone may include more than three heating zones, or more than four heating zones, or more than five heating zones, or more than six heating zones. The oxygen-containing heating occurs in at least one oxygen-containing heating zone, optionally the at least one oxygen-containing heating zone may include two, three, four, five, six, seven or eight heating zones. The at least one oxygen-containing heating zone may include more than three heating zones, or more than four heating zones, or more than five heating zones, or more than six heating zones.

As specified above, the first period of time during which the catalyst precursor is maintained under inert gas heating must be sufficient time to convert substantially all of the silver in the silver containing compound to metallic silver and to decompose and remove substantially all organic materials. The same parameters for heating times and temperatures set forth above, apply in this embodiment as well.

After heat treating in this way, the catalyst can be used in the production of ethylene oxide. Generally, the commercially practiced ethylene oxide production processes are carried out by continuously contacting an oxygen containing gas with ethylene in the presence of the present catalysts at a temperature in the range from about 180° C. to about 330° C. and preferably about 200° C. to about 325° C., more preferably from about 225° C. to about 270° C., at a pressure which may vary from about atmospheric pressure to about 30 atmospheres depending on the mass velocity and productivity desired. Pressures in the range from about atmospheric to about 500 psi are generally employed. Higher pressures may, however, be employed within the scope of the invention. Residence times in large-scale reactors are generally on the order of about 0.1-5 seconds. Oxygen may be supplied to the reaction in an oxygen containing stream, such as air or as oxygen from a commercially available delivery source such as a tank. The resulting ethylene oxide is separated and recovered from the reaction products using conventional methods. However, for this invention, the ethylene oxide process envisions the normal gas recycle encompassing carbon dioxide recycle in the normal concentrations, e.g., up to about 10 volume percent. A usual process for the oxidation of ethylene to ethylene oxide comprises the vapor phase oxidation of ethylene with molecular oxygen in the presence of a catalyst in a fixed bed, tubular reactor. Conventional commercial fixed bed ethylene oxide reactors are typically in the form of a plurality of parallel elongated tubes (in a suitable shell) approximately 0.7 to 2.7 inches O.D. and 0.5 to 2.5 inches I.D. and 15-45 feet long filled with catalyst.

The catalysts employed herein have been shown to be particularly selective catalysts in the oxidation of ethylene with molecular oxygen to ethylene oxide. The conditions for carrying out such an oxidation reaction in the presence of the catalysts of the present invention broadly comprise those described in the prior art. This applies, for example, to suitable temperatures, pressures, residence times, diluent materials such as nitrogen, carbon dioxide, steam, argon, methane or other saturated hydrocarbons, the presence or absence of moderating agents to control the catalytic action, for example, 1,2-dichloroethane, vinyl chloride or chlorinated polyphenyl compounds, the desirability of employing recycle operations or applying successive conversion in different reactors to increase the yields of ethylene oxide, and any other special conditions which may be selected in processes for preparing ethylene oxide. Molecular oxygen employed as a reactant may be obtained from conventional sources. The suitable oxygen charge may be relatively pure oxygen, a concentrated oxygen stream comprising oxygen in major amount with lesser amounts of one or more diluents such as nitrogen, argon, etc., or another oxygen containing stream such as air. The use of the present catalysts in ethylene oxidation reactions is in no way limited to the use of specific conditions among those which are known to be effective.

The resulting ethylene oxide is separated and recovered from the reaction products by conventional methods known and used in the art. Use of the silver catalysts described herein in ethylene oxide production processes gives higher overall ethylene oxidation selectivities to ethylene oxide at a given ethylene conversion than are possible with conventional catalysts.

In the production of ethylene oxide, reactant feed mixtures may contain from about 0.5 to about 45% ethylene and from about 3 to about 15% oxygen, with the balance comprising comparatively inert materials including such substances as nitrogen, carbon dioxide, methane, ethane, argon and the like. In a preferred application of the silver catalysts of the invention, ethylene oxide is produced when an oxygen containing gas of about 95% or more of oxygen is employed. Only a portion of the ethylene usually is reacted per pass over the catalyst and after separation of the desired ethylene oxide product and the removal of appropriate purge stream and carbon dioxide to prevent uncontrolled build up of inerts and/or by-products, unreacted materials are returned to the oxidation reactor. For purposes of illustration only, the following are conditions that are often used in current commercial ethylene oxide reactor units:

GHSV 1500-10,000, inlet pressure 150-400 psig, inlet feed: ethylene 1-40%, $O_2$ 3-12%, $CO_2$ 0.1%-20%, ethane 0-3%.
Argon and/or methane and/or nitrogen.
0.3-20 ppmv total diluent chlorohydrocarbon moderator.
Coolant temperature 180-315° C.
Catalyst temperature 180° C.
$O_2$ conversion level 10-60%.
EO Production (Work Rate) 2-16 lbs. EO/cu. ft. catalyst/hr.

EXAMPLES

The invention will now be described in more detail with respect to the following non-limiting (hypothetical) example.

An epoxidation catalyst precursor is prepared as described above by depositing on an inert support a catalytically effective amount of a silver containing compound, a promoting amount of an alkali metal containing compound, and a promoting amount of a transition metal containing compound.

The catalyst precursor is then heated using a multi-zone furnace, as described above. The catalyst precursor is placed on a moving belt, which travels into the furnace at ambient temperature and then passed to a preheating zone where the temperature is raised to 90° C. Then the catalyst precursor is heated to and maintained at 450° C. in a $N_2$ gas atmosphere for the 9 minutes that it takes for the moving belt to pass through five separate heating zones, each of the heating zones being supplied with a $N_2$ gas atmosphere; at the end of the five $N_2$-supplied heating zones substantially all of the silver compound on the surface of the catalyst precursor is converted to silver and substantially all of the organic materials and organic complexes are being decomposed.

After the $N_2$-supplied heating zones, there are two separate oxygen-containing heating zones having a temperature of 500° C.; each of these two heating zones being supplied with an oxygen-containing atmosphere. It takes 4 minutes for the belt to move through these heating zones, after which the moving belt and catalyst/catalyst precursor enters into a $N_2$ gas atmosphere cooling zone where it is gradually returned to ambient temperature.

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A process for the preparation of a catalyst useful for the vapor phase production of ethylene oxide from ethylene and oxygen comprising:
    providing a catalyst precursor comprising an inert support having a catalytically effective amount of a silver containing compound, a promoting amount of an alkali metal containing compound, and a promoting amount of a transition metal containing compound disposed thereon; and
    heating the catalyst precursor for a first period of time in an inert gas atmosphere and at a first temperature range from about 25° C. to about 600° C., and continuing said heating for a second period of time in an oxygen-containing atmosphere and at a second temperature range from about 350° C. to about 600° C.

2. The process of claim 1 wherein the inert support comprises alpha alumina.

3. The process of claim 1 wherein the silver containing compound comprises silver oxalate, silver nitrate, silver oxide, silver carbonate, a silver carboxylate, silver citrate, silver phthalate, silver lactate, silver propionate, silver butyrate, silver fatty acid salts, and combinations thereof.

4. The process of claim 1 wherein the providing the catalyst precursor further comprises a component selected from the group consisting of amines, alcohols, ammonia, lactic acid and combinations thereof.

5. The process of claim 1 wherein the alkali metal containing compound comprises cesium.

6. The process of claim 1 wherein the transition metal comprises an element selected from Groups 5b, 6b, 7b and 8 of the Periodic Table of the Elements, and combinations thereof.

7. The process of claim 1 wherein the transition metal comprises an element selected from Group 7b of the Periodic Table of the Elements, and combinations thereof.

8. The process of claim 1 wherein the transition metal comprises rhenium.

9. The process of claim 1 wherein the inert gas atmosphere comprises nitrogen, argon, krypton, helium, or combinations thereof.

10. The process of claim 1 wherein the length of the first period of time is from about 1 minute to about 45 minutes.

11. The process of claim 1 wherein the length of the second period of time is from about 0.5 minutes to about 45 minutes.

12. The process of claim 1 wherein the temperature during the first period of time is from about 25° C. to about 550° C.

13. The process of claim 1 wherein the length of the first period of time is from about 5 minutes to about 40 minutes, and the length of the second period of time is from about 1 minute to about 35 minutes.

14. The process of claim 1 wherein the first period of time is longer than the second period of time.

15. The process of claim 1 wherein said oxygen-containing atmosphere comprises molecular oxygen, $CO_2$, NO, $NO_2$, $N_2O_3$, $N_2O_4$, or $N_2O_5$, or a substance capable of forming NO, $NO_2$, $N_2O_3$, $N_2O_4$, or $N_2O_5$ under calcining conditions, or combinations thereof, and optionally comprising $SO_3$, $SO_2$, $P_2O_5$, $P_2O_3$ or combinations thereof.

16. The process of claim 1 wherein the oxygen-containing atmosphere comprises at least molecular oxygen.

17. A process for the preparation of a catalyst useful for the vapor phase production of ethylene oxide from ethylene and oxygen comprising:
    providing a catalyst precursor comprising an inert support having a catalytically effective amount of a silver containing compound, a promoting amount of an alkali metal containing compound, and a promoting amount of a transition metal containing compound disposed thereon; and
    heating the catalyst precursor for a first period of time in at least one inert gas heating zone under an inert gas atmosphere at a temperature range of about 25° C. to about 600° C., and continuing said heating for a second period of time in at least one oxygen-containing heating zone having an oxygen-containing atmosphere at a temperature range of about 350° C. to about 600° C., wherein the first period of time is sufficient to convert the silver in the silver containing compound to metallic silver and to decompose and remove organic materials.

18. The process of claim 17 wherein the first period of time is longer than the second period of time.

19. The process of claim 17 wherein the at least one inert gas heating zone comprises more than three heating zones.

20. The process of claim 17 wherein the at least one inert gas heating zone comprises more than three heating zones, and the at least one oxygen-containing heating zone contains two heating zones.

21. The process of claim 17 wherein the inert support comprises alpha alumina, the silver containing compound comprises silver oxalate, silver nitrate, silver oxide, silver carbonate, a silver carboxylate, silver citrate, silver phthalate, silver lactate, silver propionate, silver butyrate, silver fatty acid salts, and combinations thereof, the alkali metal containing compound comprises cesium, the transition metal comprises an element selected from Group 7b of the Periodic Table of the Elements, and combinations thereof, the transition metal comprises rhenium.

22. The process of claim 17 wherein the length of the first period of time is from about 5 minutes to about 40 minutes.

23. The process of claim 17 wherein the length of the second period of time is from about 1 minute to about 35 minutes.

24. The process of claim 17 wherein the temperature during the first period of time is from about 25° C. to about 500° C.

* * * * *